(12) United States Patent
Zammataro et al.

(10) Patent No.: US 9,775,623 B2
(45) Date of Patent: Oct. 3, 2017

(54) SURGICAL CLIP APPLIER INCLUDING CLIP RELIEF FEATURE

(75) Inventors: Thomas Zammataro, Hamden, CT (US); Brian J. Creston, West Haven, CT (US)

(73) Assignee: Covidien LP, Mansfield, MA (US)

( * ) Notice: Subject to any disclaimer, the term of this patent is extended or adjusted under 35 U.S.C. 154(b) by 1579 days.

(21) Appl. No.: 13/405,386

(22) Filed: Feb. 27, 2012

(65) Prior Publication Data

US 2012/0277765 A1 Nov. 1, 2012

Related U.S. Application Data

(60) Provisional application No. 61/480,432, filed on Apr. 29, 2011.

(51) Int. Cl.
*A61B 17/10* (2006.01)
*A61B 17/128* (2006.01)
*A61B 17/072* (2006.01)
*A61B 17/068* (2006.01)

(52) U.S. Cl.
CPC ........ *A61B 17/1285* (2013.01); *A61B 17/068* (2013.01); *A61B 17/072* (2013.01); *A61B 17/07207* (2013.01); *A61B 17/128* (2013.01)

(58) Field of Classification Search
CPC . A61B 17/128; A61B 17/1285; A61B 17/068; A61B 17/072; A61B 17/07207
See application file for complete search history.

(56) References Cited

U.S. PATENT DOCUMENTS

| 3,120,230 A | 2/1964 | Skold |
| 3,638,847 A | 2/1972 | Noiles et al. |
| 3,675,688 A | 7/1972 | Bryan et al. |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |

(Continued)

FOREIGN PATENT DOCUMENTS

| AU | 2010200641 A1 | 10/2010 |
| CA | 2740831 A1 | 4/2010 |

(Continued)

OTHER PUBLICATIONS

Chinese First Office Action corresponding to counterpart Int'l Appln. No. CN 201210586826.1 dated Dec. 30, 2015.

(Continued)

*Primary Examiner* — Diane Yabut

(57) ABSTRACT

A surgical clip applier includes a jaw assembly having first and second jaws. Each jaw defines an opposed surface configured to receive a portion of a surgical clip. The jaws are moveable between a spaced-apart position and an approximated position for forming the surgical clip about tissue. Each jaw includes a relief element disposed on a surface adjacent to and substantially transverse relative to the opposed surface thereof. The relief elements are cooperable to define a relief recess upon movement of the jaws to the approximated position. The relief recess is configured to receive at least a portion of a previously formed surgical clip during formation of a subsequent surgical clip about tissue adjacent to the previously formed surgical clip.

16 Claims, 7 Drawing Sheets

(56) References Cited

U.S. PATENT DOCUMENTS

| | | | |
|---|---|---|---|
| 4,412,539 | A | 11/1983 | Jarvik |
| 4,449,531 | A | 5/1984 | Cerwin et al. |
| 4,478,220 | A | 10/1984 | Di Giovanni et al. |
| 4,480,640 | A | 11/1984 | Becht |
| 4,480,641 | A | 11/1984 | Failla et al. |
| 4,487,204 | A | 12/1984 | Hrouda |
| 4,487,205 | A | 12/1984 | Di Giovanni et al. |
| 4,491,133 | A | 1/1985 | Menges et al. |
| 4,492,232 | A | 1/1985 | Green |
| 4,498,476 | A | 2/1985 | Cerwin et al. |
| 4,500,024 | A | 2/1985 | DiGiovanni et al. |
| 4,509,518 | A * | 4/1985 | McGarry ............ A61B 17/128 606/143 |
| 4,512,345 | A | 4/1985 | Green |
| 4,522,207 | A | 6/1985 | Klieman et al. |
| 4,532,925 | A | 8/1985 | Blake, III |
| 4,534,351 | A | 8/1985 | Rothfuss et al. |
| 4,545,377 | A | 10/1985 | Cerwin et al. |
| 4,549,544 | A | 10/1985 | Favaron |
| 4,556,058 | A | 12/1985 | Green |
| 4,557,263 | A | 12/1985 | Green |
| 4,562,839 | A | 1/1986 | Blake, III et al. |
| 4,572,183 | A | 2/1986 | Juska |
| 4,576,165 | A | 3/1986 | Green et al. |
| 4,576,166 | A | 3/1986 | Montgomery |
| 4,590,937 | A | 5/1986 | Deniega |
| 4,592,498 | A | 6/1986 | Braun et al. |
| 4,598,711 | A | 7/1986 | Deniega |
| 4,602,631 | A | 7/1986 | Funatsu |
| 4,611,595 | A | 9/1986 | Klieman et al. |
| 4,612,932 | A | 9/1986 | Caspar et al. |
| 4,616,650 | A | 10/1986 | Green et al. |
| 4,616,651 | A | 10/1986 | Golden |
| 4,624,254 | A | 11/1986 | McGarry et al. |
| 4,637,395 | A | 1/1987 | Caspar et al. |
| 4,646,740 | A | 3/1987 | Peters et al. |
| 4,647,504 | A | 3/1987 | Kimimura et al. |
| 4,658,822 | A | 4/1987 | Kees, Jr. |
| 4,660,558 | A | 4/1987 | Kees, Jr. |
| 4,662,373 | A | 5/1987 | Montgomery |
| 4,662,374 | A | 5/1987 | Blake, III |
| 4,671,278 | A | 6/1987 | Chin |
| 4,671,282 | A | 6/1987 | Tretbar |
| 4,674,504 | A | 6/1987 | Klieman et al. |
| 4,681,107 | A | 7/1987 | Kees, Jr. |
| 4,696,396 | A | 9/1987 | Samuels |
| 4,702,247 | A | 10/1987 | Blake, III et al. |
| 4,706,668 | A | 11/1987 | Backer |
| 4,712,549 | A | 12/1987 | Peters |
| 4,733,664 | A | 3/1988 | Kirsch et al. |
| 4,733,666 | A | 3/1988 | Mercer, Jr. |
| 4,759,364 | A | 7/1988 | Boebel |
| 4,765,335 | A | 8/1988 | Schmidt et al. |
| 4,777,949 | A | 10/1988 | Perlin |
| 4,777,950 | A | 10/1988 | Kees, Jr. |
| 4,796,625 | A | 1/1989 | Kees, Jr. |
| 4,799,481 | A | 1/1989 | Transue et al. |
| 4,815,466 | A | 3/1989 | Perlin |
| 4,817,604 | A | 4/1989 | Smith, III |
| 4,821,721 | A | 4/1989 | Chin et al. |
| 4,822,348 | A | 4/1989 | Casey |
| 4,827,930 | A | 5/1989 | Kees, Jr. |
| 4,834,096 | A | 5/1989 | Oh et al. |
| 4,850,355 | A | 7/1989 | Brooks et al. |
| 4,854,317 | A | 8/1989 | Braun |
| 4,856,517 | A | 8/1989 | Collins et al. |
| 4,929,239 | A | 5/1990 | Braun |
| 4,929,240 | A | 5/1990 | Kirsch et al. |
| 4,931,058 | A | 6/1990 | Cooper |
| 4,932,955 | A | 6/1990 | Merz et al. |
| 4,934,364 | A | 6/1990 | Green |
| 4,943,298 | A | 7/1990 | Fujita et al. |
| 4,951,860 | A | 8/1990 | Peters et al. |
| 4,957,500 | A | 9/1990 | Liang et al. |
| 4,966,603 | A | 10/1990 | Focelle et al. |
| 4,967,949 | A | 11/1990 | Sandhaus |
| 4,983,176 | A | 1/1991 | Cushman et al. |
| 4,988,355 | A | 1/1991 | Leveen et al. |
| 5,002,552 | A | 3/1991 | Casey |
| 5,026,379 | A | 6/1991 | Yoon |
| 5,030,224 | A | 7/1991 | Wright et al. |
| 5,030,226 | A | 7/1991 | Green et al. |
| 5,032,127 | A | 7/1991 | Frazee et al. |
| 5,035,692 | A | 7/1991 | Lyon et al. |
| 5,047,038 | A | 9/1991 | Peters et al. |
| 5,049,152 | A | 9/1991 | Simon |
| 5,049,153 | A | 9/1991 | Nakao et al. |
| 5,053,045 | A | 10/1991 | Schmidt et al. |
| 5,059,202 | A | 10/1991 | Liang et al. |
| 5,062,563 | A | 11/1991 | Green et al. |
| 5,062,846 | A | 11/1991 | Oh et al. |
| 5,078,731 | A | 1/1992 | Hayhurst |
| 5,084,057 | A | 1/1992 | Green et al. |
| 5,100,416 | A | 3/1992 | Oh et al. |
| 5,100,420 | A | 3/1992 | Green et al. |
| 5,104,394 | A | 4/1992 | Knoepfler |
| 5,104,395 | A | 4/1992 | Thornton et al. |
| 5,112,343 | A | 5/1992 | Thornton |
| 5,122,150 | A | 6/1992 | Puig |
| 5,127,915 | A | 7/1992 | Mattson |
| 5,129,885 | A | 7/1992 | Green et al. |
| 5,156,608 | A | 10/1992 | Troidl et al. |
| 5,160,339 | A | 11/1992 | Chen et al. |
| 5,163,945 | A * | 11/1992 | Ortiz ................ A61B 17/1285 227/901 |
| 5,171,247 | A | 12/1992 | Hughett et al. |
| 5,171,249 | A | 12/1992 | Stefanchik |
| 5,171,250 | A | 12/1992 | Yoon |
| 5,171,251 | A | 12/1992 | Bregen et al. |
| 5,171,252 | A | 12/1992 | Friedland |
| 5,171,253 | A | 12/1992 | Klieman |
| 5,192,288 | A | 3/1993 | Thompson et al. |
| 5,197,970 | A | 3/1993 | Green et al. |
| 5,199,566 | A | 4/1993 | Ortiz et al. |
| 5,201,746 | A | 4/1993 | Shichman |
| 5,201,900 | A | 4/1993 | Nardella |
| 5,207,691 | A | 5/1993 | Nardella |
| 5,207,692 | A | 5/1993 | Kraus et al. |
| 5,217,473 | A | 6/1993 | Yoon |
| 5,219,353 | A | 6/1993 | Garvey, III et al. |
| 5,246,450 | A | 9/1993 | Thornton et al. |
| 5,269,792 | A | 12/1993 | Kovac et al. |
| 5,281,228 | A | 1/1994 | Wolfson |
| 5,282,807 | A | 2/1994 | Knoepfler |
| 5,282,808 | A | 2/1994 | Kovac et al. |
| 5,282,832 | A | 2/1994 | Toso et al. |
| 5,289,963 | A | 3/1994 | McGarry et al. |
| 5,290,299 | A | 3/1994 | Fain et al. |
| 5,300,081 | A | 4/1994 | Young et al. |
| 5,304,183 | A | 4/1994 | Gourlay et al. |
| 5,306,280 | A | 4/1994 | Bregen et al. |
| 5,306,283 | A | 4/1994 | Conners |
| 5,312,426 | A | 5/1994 | Segawa et al. |
| 5,330,442 | A | 7/1994 | Green et al. |
| 5,330,487 | A | 7/1994 | Thornton et al. |
| 5,340,360 | A | 8/1994 | Stefanchik |
| 5,342,373 | A | 8/1994 | Stefanchik et al. |
| 5,354,304 | A | 10/1994 | Allen |
| 5,354,306 | A | 10/1994 | Garvey, III et al. |
| 5,366,458 | A | 11/1994 | Korthoff et al. |
| 5,366,459 | A | 11/1994 | Yoon |
| 5,368,600 | A | 11/1994 | Failla et al. |
| 5,381,943 | A | 1/1995 | Allen et al. |
| 5,382,253 | A | 1/1995 | Hogendijk |
| 5,382,254 | A | 1/1995 | McGarry |
| 5,382,255 | A | 1/1995 | Castro |
| 5,383,880 | A | 1/1995 | Hooven |
| 5,383,881 | A | 1/1995 | Green |
| 5,395,375 | A | 3/1995 | Turkel et al. |
| 5,395,381 | A | 3/1995 | Green |
| 5,403,327 | A | 4/1995 | Thornton et al. |
| 5,409,498 | A | 4/1995 | Braddock et al. |
| 5,413,584 | A | 5/1995 | Scjulze |
| 5,423,835 | A | 6/1995 | Green |

(56) References Cited

U.S. PATENT DOCUMENTS

| | | |
|---|---|---|
| 5,425,740 A | 6/1995 | Hutchinson, Jr. |
| 5,431,667 A | 7/1995 | Thompson |
| 5,431,668 A | 7/1995 | Burbank, III et al. |
| 5,431,669 A | 7/1995 | Thompson |
| 5,439,468 A | 8/1995 | Schulze et al. |
| 5,441,509 A | 8/1995 | Vidal |
| 5,447,513 A | 9/1995 | Davison et al. |
| 5,449,365 A | 9/1995 | Green |
| 5,462,555 A | 10/1995 | Bolanos |
| 5,462,558 A | 10/1995 | Kolesa |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips |
| 5,514,149 A | 5/1996 | Green |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green |
| 5,527,320 A | 6/1996 | Carruthers et al. |
| 5,542,949 A | 8/1996 | Yoon |
| 5,547,474 A | 8/1996 | Kloeckl |
| 5,569,274 A | 10/1996 | Rapacki et al. |
| 5,571,121 A | 11/1996 | Heifetz |
| 5,575,802 A | 11/1996 | McQuildin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A * | 3/1997 | Pratt .................. A61B 17/1285 227/901 |
| 5,618,291 A | 4/1997 | Thompson |
| 5,618,306 A | 4/1997 | Roth et al. |
| 5,620,452 A | 4/1997 | Yoon |
| 5,626,585 A | 5/1997 | Mittelstadt |
| 5,626,586 A | 5/1997 | Pistl et al. |
| 5,626,587 A | 5/1997 | Bishop et al. |
| 5,626,592 A | 5/1997 | Phillips |
| RE35,525 E | 6/1997 | Stefanchik et al. |
| 5,634,930 A | 6/1997 | Thornton et al. |
| 5,643,291 A | 7/1997 | Pier |
| 5,645,551 A | 7/1997 | Green |
| 5,645,553 A | 7/1997 | Kolesa |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier |
| 5,695,505 A | 12/1997 | Yoon |
| 5,697,938 A | 12/1997 | Jensen et al. |
| 5,700,270 A | 12/1997 | Peyser |
| 5,700,271 A | 12/1997 | Whitfield |
| 5,702,048 A | 12/1997 | Eberlin |
| 5,709,706 A | 1/1998 | Kienzle et al. |
| 5,713,911 A | 2/1998 | Racenet |
| 5,713,912 A | 2/1998 | Porter |
| 5,720,756 A | 2/1998 | Green |
| 5,722,982 A | 3/1998 | Ferreira et al. |
| 5,725,537 A | 3/1998 | Green |
| 5,725,538 A | 3/1998 | Green |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt |
| 5,766,189 A | 6/1998 | Matsuno |
| 5,769,857 A | 6/1998 | Reztzov et al. |
| 5,772,673 A | 6/1998 | Cuny |
| 5,776,146 A | 7/1998 | Sackier et al. |
| 5,776,147 A | 7/1998 | Dolendo |
| 5,779,718 A | 7/1998 | Green |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts |
| 5,792,150 A | 8/1998 | Pratt |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield |
| 5,833,700 A | 11/1998 | Fogelberg et al. |
| 5,835,199 A | 11/1998 | Phillips |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser |
| 5,868,761 A | 2/1999 | Nicholas |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare |
| 5,906,625 A | 5/1999 | Bito et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser |
| 5,951,574 A | 9/1999 | Stefanchik et al. |
| 5,972,003 A | 10/1999 | Rousseau |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,009,551 A | 4/2000 | McKean et al. |
| RE36,720 E | 5/2000 | Green |
| 6,059,799 A | 5/2000 | Aranyi |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis |
| 6,537,289 B1 | 3/2003 | Kayan |
| 6,546,935 B2 | 4/2003 | Hooven |
| 6,551,333 B2 | 4/2003 | Kuhns et al. |
| 6,562,051 B1 | 5/2003 | Bolduc et al. |

(56) References Cited

U.S. PATENT DOCUMENTS

| | | |
|---|---|---|
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan |
| 6,676,659 B2 | 1/2004 | Hutchins et al. |
| 6,679,894 B2 | 1/2004 | Damarati |
| RE38,445 E | 2/2004 | Pistl |
| 6,695,854 B1 | 2/2004 | Kayan |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 * | 5/2006 | Hughett ............ A61B 17/1285 606/139 |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield |
| 7,644,848 B2 | 1/2010 | Swayze et al. |
| 7,695,482 B2 | 4/2010 | Viola |
| 7,717,926 B2 | 5/2010 | Whitfield |
| 7,727,248 B2 | 6/2010 | Smith et al. |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield |
| 7,887,553 B2 | 2/2011 | Lehman et al. |
| 7,905,890 B2 | 3/2011 | Whitfield |
| 7,942,885 B2 | 5/2011 | Sixto, Jr. et al. |
| 7,952,060 B2 | 5/2011 | Watanabe et al. |
| 7,963,433 B2 | 6/2011 | Whitman et al. |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich |
| 8,021,378 B2 | 9/2011 | Sixto, Jr. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin |
| 8,088,061 B2 | 1/2012 | Wells |
| 8,091,755 B2 | 1/2012 | Kayan |
| 8,100,926 B1 | 1/2012 | Filshie et al. |
| 8,128,643 B2 | 3/2012 | Aranyi |
| 8,133,240 B2 | 3/2012 | Damarati |
| 8,142,451 B2 | 3/2012 | Boulnois |
| 8,157,145 B2 | 4/2012 | Shelton, IV et al. |
| 8,157,149 B2 | 4/2012 | Olson |
| 8,157,151 B2 | 4/2012 | Ingmanson |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |

(56) References Cited

U.S. PATENT DOCUMENTS

| | | |
|---|---|---|
| 8,211,124 B2 | 7/2012 | Ainsworth et al. |
| 8,216,255 B2 | 7/2012 | Smith et al. |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,272,554 B2 | 9/2012 | Whitman et al. |
| 8,282,655 B2 | 10/2012 | Whitfield |
| 8,308,743 B2 | 11/2012 | Matsuno et al. |
| 8,328,822 B2 | 12/2012 | Huitema |
| 8,336,556 B2 | 12/2012 | Zergiebel |
| 8,348,130 B2 | 1/2013 | Shah |
| 8,357,171 B2 | 1/2013 | Whitfield |
| 8,366,709 B2 | 2/2013 | Schechter et al. |
| 8,366,726 B2 | 2/2013 | Dennis |
| 8,371,491 B2 | 2/2013 | Huitema |
| 8,372,095 B2 | 2/2013 | Viola |
| 8,382,773 B2 | 2/2013 | Whitfield |
| 8,398,655 B2 | 3/2013 | Cheng et al. |
| 8,403,945 B2 | 3/2013 | Whitfield |
| 8,403,946 B2 | 3/2013 | Whitfield |
| 8,408,442 B2 | 4/2013 | Racenet et al. |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,460 B2 | 6/2013 | Yodfat et al. |
| 8,465,502 B2 | 6/2013 | Zergiebel |
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |
| 8,518,055 B1 | 8/2013 | Cardinale et al. |
| 8,523,882 B2 | 9/2013 | Huitema |
| 8,529,585 B2 | 9/2013 | Jacobs |
| 8,529,586 B2 | 9/2013 | Rosenberg |
| 8,529,588 B2 | 9/2013 | Ahlberg |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield |
| 8,585,717 B2 | 11/2013 | Sorrentino |
| 8,603,109 B2 | 12/2013 | Aranyi |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,920,438 B2 | 12/2014 | Aranyi et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,282,961 B2 | 3/2016 | Whitman et al. |
| 9,326,776 B2 | 5/2016 | Gadberry et al. |
| 9,358,011 B2 | 6/2016 | Sorrentino et al. |
| 9,358,015 B2 | 6/2016 | Sorrentino et al. |
| 9,364,216 B2 | 6/2016 | Rockrohr et al. |
| 9,364,239 B2 | 6/2016 | Malkowski |
| 9,364,240 B2 | 6/2016 | Whitfield et al. |
| 9,370,400 B2 | 6/2016 | Parihar |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,480,477 B2 | 11/2016 | Aranyi et al. |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0208231 A1 | 11/2003 | Williamson, IV et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |

(56) References Cited

U.S. PATENT DOCUMENTS

| | | |
|---|---|---|
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1* | 4/2006 | Whitfield ............ A61B 17/10 606/142 |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson, Jr. et al. |
| 2006/0224165 A1 | 10/2006 | Surti |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santili et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0083813 A1 | 4/2008 | Zemlok et al. |
| 2008/0103510 A1 | 5/2008 | Taylor et al. |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |

(56) References Cited

U.S. PATENT DOCUMENTS

| | | |
|---|---|---|
| 2008/0255413 A1 | 10/2008 | Zemlok et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0222003 A1 | 9/2009 | Otley et al. |
| 2009/0228023 A1 | 9/2009 | Cui et al. |
| 2009/0228024 A1 | 9/2009 | Whitfield et al. |
| 2009/0264904 A1 | 10/2009 | Aldrich et al. |
| 2009/0299382 A1 | 12/2009 | Zergiebel |
| 2009/0326558 A1 | 12/2009 | Cui et al. |
| 2010/0049216 A1 | 2/2010 | Zergiebel |
| 2010/0057102 A1 | 3/2010 | Sorrentino et al. |
| 2010/0057103 A1 | 3/2010 | Sorrentino et al. |
| 2010/0057104 A1 | 3/2010 | Sorrentino et al. |
| 2010/0057105 A1 | 3/2010 | Sorrentino |
| 2010/0057106 A1 | 3/2010 | Sorrentino et al. |
| 2010/0057107 A1 | 3/2010 | Sorrentino et al. |
| 2010/0069935 A1 | 3/2010 | Crainich |
| 2010/0121351 A1 | 5/2010 | Whitfield |
| 2010/0137886 A1 | 6/2010 | Zergiebel |
| 2010/0204715 A1 | 8/2010 | Whitfield et al. |
| 2010/0222790 A1 | 9/2010 | Whitfield et al. |
| 2010/0274262 A1 | 10/2010 | Schulz et al. |
| 2010/0274264 A1 | 10/2010 | Schulz et al. |
| 2011/0028994 A1 | 2/2011 | Whitfield et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087242 A1 | 4/2011 | Pribanic |
| 2011/0087243 A1 | 4/2011 | Nguyen et al. |
| 2011/0112552 A1 | 5/2011 | Lehman et al. |
| 2011/0137323 A1 | 6/2011 | Malkowski |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0029533 A1 | 2/2012 | Whitfield et al. |
| 2012/0029534 A1 | 2/2012 | Whitfield |
| 2012/0041455 A1 | 2/2012 | Martinez |
| 2012/0042497 A1 | 2/2012 | Zergiebel |
| 2012/0046671 A1 | 2/2012 | Matsuoka et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino |
| 2012/0123446 A1 | 5/2012 | Aranyi |
| 2012/0197269 A1 | 8/2012 | Zammataro |
| 2012/0265220 A1 | 10/2012 | Menn |
| 2012/0277765 A1 | 11/2012 | Zammataro |
| 2012/0330326 A1 | 12/2012 | Creston |
| 2013/0110135 A1 | 5/2013 | Whitfield |
| 2013/0131697 A1 | 5/2013 | Hartoumbekis |
| 2013/0165951 A1 | 6/2013 | Blake, III |
| 2013/0172910 A1 | 7/2013 | Malkowski |
| 2013/0172911 A1 | 7/2013 | Rockrohr |
| 2013/0172912 A1 | 7/2013 | Whitfield |
| 2013/0185952 A1 | 7/2013 | Christ |
| 2013/0190779 A1 | 7/2013 | Whitfield |
| 2013/0190780 A1 | 7/2013 | Whitfield |
| 2013/0253541 A1 | 9/2013 | Zergiebel |
| 2013/0274767 A1 | 10/2013 | Sorrentino |
| 2013/0289583 A1 | 10/2013 | Zergiebel |
| 2013/0296891 A1 | 11/2013 | Hartoumbekis |
| 2013/0296892 A1 | 11/2013 | Sorrentino |
| 2013/0310849 A1 | 11/2013 | Malkowski |
| 2013/0325040 A1 | 12/2013 | Zammataro |
| 2014/0005693 A1 | 1/2014 | Shelton, IV et al. |
| 2014/0039526 A1 | 2/2014 | Malkowski |
| 2014/0052157 A1 | 2/2014 | Whitfield |
| 2014/0058412 A1 | 2/2014 | Aranyi |
| 2014/0194903 A1 | 7/2014 | Malkowski et al. |
| 2014/0207156 A1 | 7/2014 | Malkowski |
| 2014/0296879 A1 | 10/2014 | Menn et al. |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0045816 A1 | 2/2015 | Aranyi et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0164511 A1 | 6/2015 | Whitfield et al. |
| 2015/0190138 A1 | 7/2015 | Whitfield et al. |
| 2015/0190139 A1 | 7/2015 | Zammataro |
| 2015/0282808 A1 | 10/2015 | Sorrentino et al. |
| 2015/0351771 A1 | 12/2015 | Malkowski et al. |
| 2015/0351772 A1 | 12/2015 | Malkowski et al. |
| 2016/0030044 A1 | 2/2016 | Zammataro |
| 2016/0030045 A1 | 2/2016 | Malkowski et al. |
| 2016/0113655 A1 | 4/2016 | Holsten |
| 2016/0151071 A1 | 6/2016 | Tokarz et al. |
| 2016/0192940 A1 | 7/2016 | Gokharu |
| 2016/0213377 A1 | 7/2016 | Shankarsetty |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |

FOREIGN PATENT DOCUMENTS

| | | |
|---|---|---|
| CN | 1994236 A | 7/2007 |
| CN | 101401737 A | 4/2009 |
| CN | 101530340 A | 9/2009 |
| CN | 100571640 C | 12/2009 |
| CN | 101658437 A | 3/2010 |
| CN | 101664329 A | 3/2010 |
| CN | 101664331 A | 3/2010 |
| CN | 201683954 U | 12/2010 |
| CN | 103083059 A | 5/2013 |
| CN | 103181809 A | 7/2013 |
| CN | 103181810 A | 7/2013 |
| CN | 104487006 A | 4/2015 |
| DE | 20 2009 006113 | 7/2009 |
| EP | 0 073 655 A1 | 3/1983 |
| EP | 0 085 931 A2 | 8/1983 |
| EP | 0 086 721 | 8/1983 |
| EP | 0 089 737 A1 | 9/1983 |
| EP | 0 324 166 A2 | 7/1989 |
| EP | 0 392 750 A1 | 10/1990 |
| EP | 0 406 724 A1 | 1/1991 |
| EP | 0 409 569 A1 | 1/1991 |
| EP | 0 569 223 | 11/1993 |
| EP | 0 594 003 | 4/1994 |
| EP | 0 598 529 A2 | 5/1994 |
| EP | 0 769 275 A1 | 5/1994 |
| EP | 0 622 049 A1 | 11/1994 |
| EP | 0 685 204 A1 | 12/1995 |
| EP | 0 732 078 A2 | 9/1996 |

(56) References Cited

FOREIGN PATENT DOCUMENTS

| | | |
|---|---|---|
| EP | 0 755 655 A2 | 1/1997 |
| EP | 0 760 230 A1 | 3/1997 |
| EP | 0 769 274 | 4/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 468 653 A2 | 10/2004 |
| EP | 1 609 427 A1 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 813 207 A1 | 8/2007 |
| EP | 1 894 531 A2 | 3/2008 |
| EP | 1 908 423 | 4/2008 |
| EP | 1 908 423 A2 | 4/2008 |
| EP | 1 913 881 A1 | 4/2008 |
| EP | 1 939 231 A1 | 7/2008 |
| EP | 2 000 102 A2 | 12/2008 |
| EP | 2 140 817 A1 | 1/2010 |
| EP | 2 229 895 A1 | 9/2010 |
| EP | 2 263 570 A1 | 12/2010 |
| EP | 2 332 471 | 6/2011 |
| EP | 2 412 318 A2 | 2/2012 |
| EP | 2 412 319 A2 | 2/2012 |
| EP | 2 752 165 A2 | 7/2014 |
| GB | 1134832 A | 11/1968 |
| GB | 2073022 A | 10/1981 |
| GB | 2 132 899 A | 7/1984 |
| JP | 10-118083 A | 5/1998 |
| JP | 2003 033361 A | 2/2003 |
| JP | 2006-501954 A | 1/2006 |
| JP | 2006-154230 A | 6/2006 |
| JP | 2006-209948 A | 8/2006 |
| JP | 2006-277221 A | 10/2006 |
| JP | 2007-250843 A | 9/2007 |
| JP | 2008-017876 A | 1/2008 |
| JP | 2008-047498 A | 2/2008 |
| JP | 2008-055165 A | 3/2008 |
| JP | 2008-515550 A | 5/2008 |
| JP | 2009-198991 A | 9/2009 |
| JP | 54-99386 B2 | 5/2014 |
| WO | 01/65997 A2 | 9/2001 |
| WO | WO 01/66001 | 9/2001 |
| WO | WO 01/67965 | 9/2001 |
| WO | WO 03/086207 | 10/2003 |
| WO | WO 03/092473 | 11/2003 |
| WO | 2004-032762 A1 | 4/2004 |
| WO | WO 2005/091457 A1 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | 2008/127968 A2 | 10/2008 |
| WO | WO 2008/118928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
Extended European Search Report corresponding to EP 10 25 2112.7, completed Jul. 29, 2014 and dated Aug. 5, 2014; (8 pages).
Extended European Search Report corresponding to EP 14 15 1673.2, completed Apr. 25, 2014 and dated May 8, 2014; (8 pages).
European Search Report (6 pages) for corresponding EP12165891—dated Jun. 20, 2012.
Extended European Search Report corresponding to EP 12 19 8745.7, completed Mar. 19, 2013 and dated Apr. 11, 2013; (8 pp).
Extended European Search Report corresponding to EP 12 15 2989.5, completed Apr. 9, 2013 and dated Apr. 18, 2013; (9 pp).
Extended European Search Report corresponding to EP 08 73 2820.9, completed Jul. 2, 2013 and dated Jul. 9, 2013; (10 pp).
Extended European Search Report corresponding to EP 12 19 1706.6, completed Dec. 19, 2012 and dated Jan. 8, 2013; (6 pp).
Extended European Search Report corresponding to EP 13 17 2008.8, completed Aug. 14, 2013 and dated Aug. 28, 2013; (8 pp).
Extended European Search Report corresponding to EP 13 16 6382.5, completed Nov. 19, 2013 and dated Nov. 28, 2013; (8 pp).
Extended European Search Report corresponding to EP 11 25 0194.5, completed Nov. 25, 2013 and dated Dec. 3, 2013; (8 pp).
Extended European Search Report corresponding to EP 10 25 1798.4, completed Dec. 12, 2013 and dated Jan. 2, 2014; (9 pp).
The extended International Search Report corresponding to European Application No. 07 25 3905.9, dated Jan. 29, 2008; dated Feb. 7, 2008; (7 Pages).
The partial International Search Report corresponding to European Application No. EP 07 25 3807.7, dated Jul. 23, 2008; dated Aug. 1, 2008; (3 pages).
International Search Report corresponding to International Application No. PCT/US08/58185, dated Sep. 4, 2008; dated Sep. 9, 2008; (2 Pages).
The International Search Report corresponding to International Application No. PCT/US08/59859, dated Sep. 14, 2008; dated Sep. 18, 2008; (2 Pages).
The extended European Search Report corresponding to European Application No. EP 07 25 3807.7, dated Nov. 7, 2008; dated Nov. 26, 2008; (11 Pages).
The extended European Search Report corresponding to European Application No. EP 09252049.3, dated Dec. 11, 2009; dated Jan. 12, 2010; (3 Pages).
The extended European Search Report corresponding to European Application No. EP 09252050.1, dated Dec. 23, 2009; dated Jan. 21, 2010; (3 Pages).
The extended European Search Report corresponding to European Application No. EP 09252051.9, dated Dec. 21, 2009; dated Jan. 28, 2010; (3 Pages).

(56) References Cited

OTHER PUBLICATIONS

The extended European Search Report corresponding to European Application No. EP 09252052.7, dated Nov. 16, 2009; dated Nov. 24, 2009; (3 Pages).
The extended European Search Report corresponding to European Application No. EP 09252053.5; dated Nov. 24, 2009; dated Dec. 1, 2009; (3 Pages).
The extended European Search Report corresponding to European Application No. EP 09252054.3, dated Jan. 7, 2010; dated Jan. 22, 2010; (3 Pages).
Extended European Search Report corresponding to European Application No. EP 09252056.8, dated Jan. 8, 2010; dated Feb. 5, 2010; (3 Pages).
Extended European Search Report corresponding to European Application No. EP 10250497.4, dated May 4, 2010; dated May 12, 2010; (6 Pages).
Extended European Search Report corresponding to European Application No. EP 10252079.8, dated Mar. 8, 2011; dated Mar. 17, 2011; (3 Pages).
European Search Report corresponding to European Application No. EP 05810218.7, dated Apr. 18, 2011; dated May 20, 2011; (3 pages).
European Search Report corresponding to European Application No. EP 05807612.6, dated May 2, 2011; dated May 20, 2011; (3 pages).
Extended European Search Report corresponding to European Application No. EP 10251737.2, dated May 9, 2011; dated May 20, 2011; (4 pages).
Extended European Search Report corresponding to European Application No. EP 11002681.2, dated May 31, 2011; dated Jun. 10, 2011; (3 Pages).
The extended European Search Report corresponding to European Application No. EP 11250214.1, dated May 25, 2011; dated Jun. 1, 2011; (3 Pages).
"Salute II Disposable Fixation Device", Technique Guide—Laparoscopic and Open Inguinal and Ventral Hernia Repair; Davol, A Bard Company, 2006; (7 Pages).
The extended European Search Report corresponding to European Application No. EP 12 16 2288.0, dated Jun. 4, 2012 and dated Jul. 7, 2012; (6 Pages).
The extended European Search Report corresponding to European Application No. EP 12 16 4955.2, dated Aug. 23, 2012 and dated Sep. 4, 2012; (5 Pages).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to Au 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
European Office Action corresponding to EP 12 152 989.5 dated May 4, 2015.
Australian Office Action corresponding to AU 2009212759 dated May 7, 2015.
Japanese Office Action corresponding to JP 2013-229070 dated May 8, 2015.
Japanese Office Action corresponding to JP 2013-229996 dated May 8, 2015.
Japanese Office Action corresponding to JP 2014-190735 dated May 27, 2015; no English translation attached—unavailable.
The extended European Search Report corresponding to European Application No. EP 12 18 6401.1, dated Nov. 22, 2012 and dated Nov. 30, 2012.
The extended European Search Report corresponding to European Application No. EP 12 18 6448.2, dated Nov. 28, 2012 and dated Dec. 10, 2012; (6 Pages).
The extended European Search Report corresponding to European Application No. EP 12 19 1706.6, dated Dec. 19, 2012 and dated Jan. 8, 2013; (6 Pages).
The extended European Search Report corresponding to European Application No. EP 11 25 0754.6, dated Oct. 22, 2012 and dated Oct. 31, 2012; (6 Pages).
European Search Report corresponding to European Application No. EP 05 80 2686.5, dated Jan. 9, 2012; dated Jan. 18, 2012; (3 Pages).
The extended European Search Report corresponding to European Application No. EP 12 15 1313.9, dated Mar. 20, 2012 and dated Apr. 12, 2012; (5 Pages).
The extended European Search Report corresponding to European Application No. EP 12 16 1291.5, dated Apr. 24, 2012 and dated May 4, 2012; (5 Pages).
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 14 15 0321.9 dated Sep. 23, 2015.
Extended European Search Report corresponding to counterpart Int'l Application No. EP 11 25 0675.3 dated Oct. 7, 2015.
Extended European Search Report corresponding to counterpart Int'l Application No. EP 11 25 0674.6 dated Oct. 7, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.

(56) References Cited

OTHER PUBLICATIONS

Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN2015/094172 dated Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
Chinese First Office Action corresponding to Int'l Appln. No. CN 201510205737.1 dated Nov. 1, 2016.
European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Extended European Search Report corresponding to Int'l Appln. No. EP 16 18 4652.2 dated Jan. 4, 2017.
Chinese First Office Action corresponding to Int'l Appln. No. CN 201510419902.3 dated Jan. 4, 2017.

\* cited by examiner

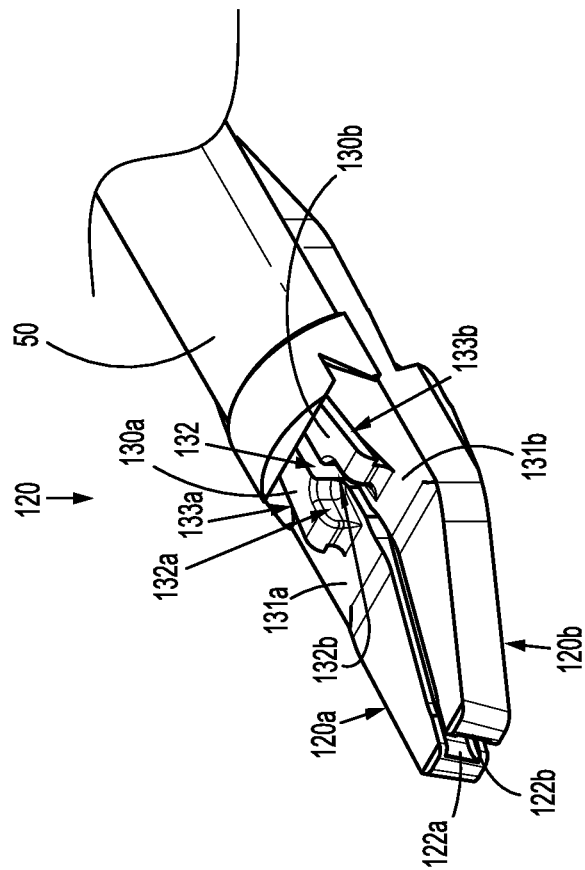
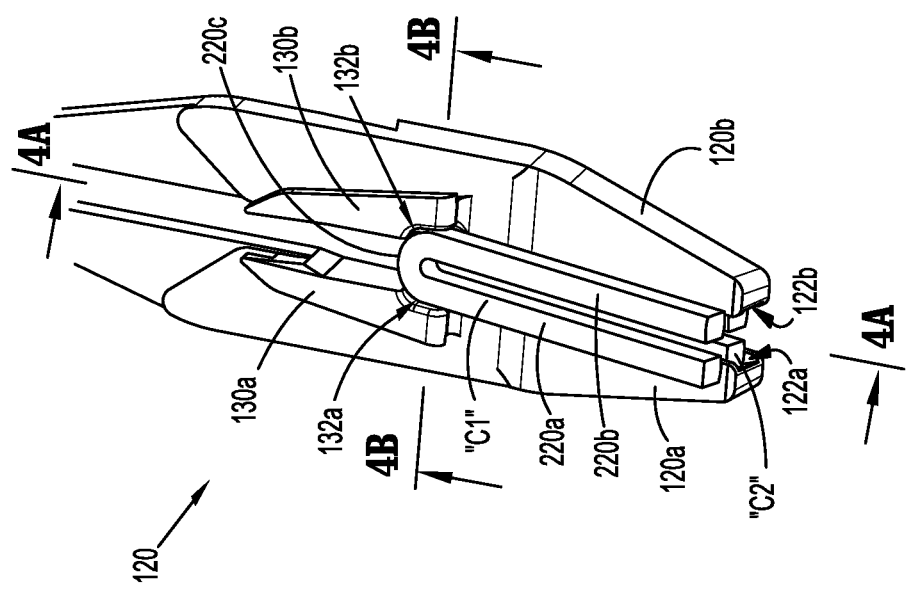

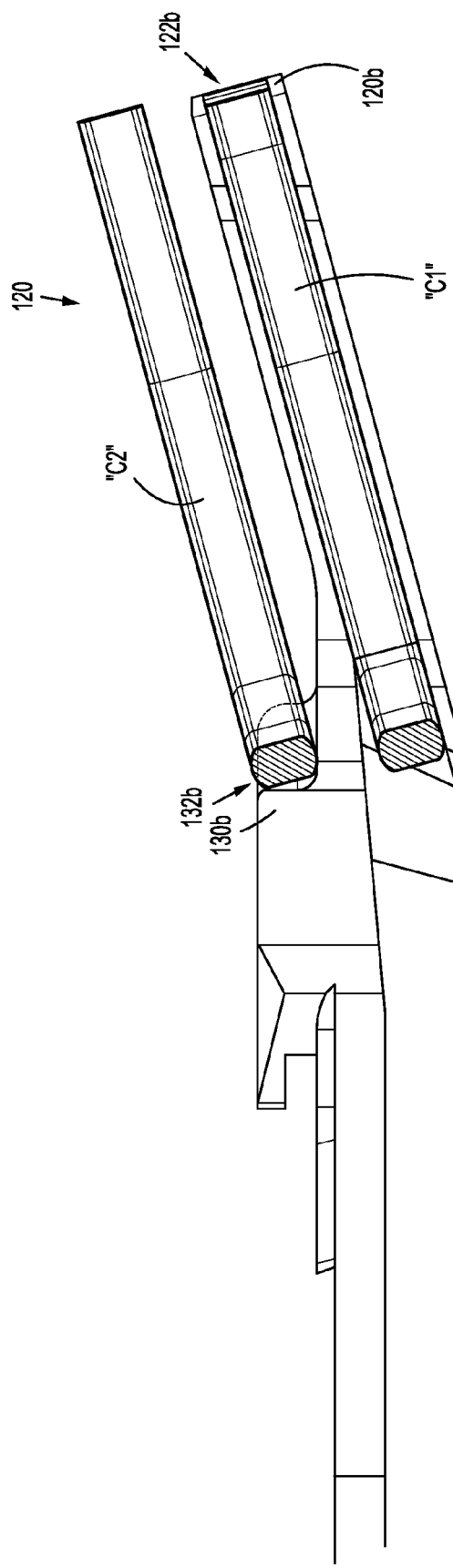
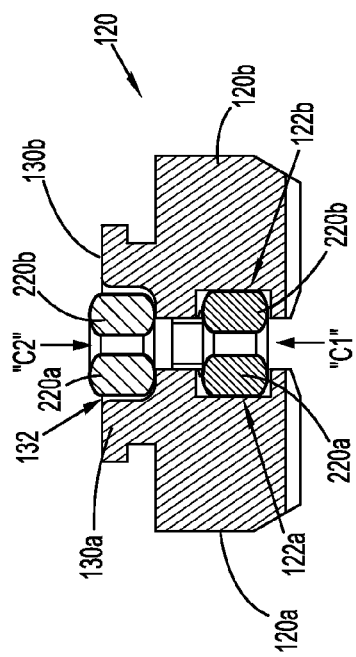
FIG. 4A
FIG. 4B

SURGICAL CLIP APPLIER INCLUDING CLIP RELIEF FEATURE

CROSS REFERENCE TO RELATED APPLICATION

The present application claims the benefit of and priority to U.S. Provisional Application Ser. No. 61/480,432, filed on Apr. 29, 2011, the entire contents of which are incorporated herein by reference.

BACKGROUND

Technical Field

The present disclosure relates to surgical instruments. More particularly, the present disclosure relates to an endoscopic surgical clip applier.

Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip or a series of clips during a surgical procedure. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity.

However, during the application of multiple clips adjacent to one another, it has been found that the previously applied clips may become lodged between the jaws during application of subsequent clips or may otherwise interfere with the application of the subsequent clips. Such an occurrence may result in formation or even dislodging of the previously applied clip, inadequate application of the subsequent clip, and/or damage to the clip applier or tissue structure. It is therefore desirable to provide a surgical clip applier that inhibits the occurrence of interference by a previously applied clip with the subsequent application of clips adjacent thereto.

SUMMARY

In accordance with one embodiment of the present disclosure, a surgical clip applier is provided. The surgical clip applier includes a jaw assembly including first and second jaws. Each jaw defines an opposed surface configured to receive a portion of a surgical clip. The jaws are moveable between a spaced-apart position and an approximated position for forming the surgical clip about tissue. Each jaw includes a relief element disposed on a surface adjacent to and substantially transverse relative to the opposed surface thereof. The relief elements are cooperable with one another to define a relief recess upon movement of the jaws to the approximated position. The relief recess is configured to receive at least a portion of a previously formed surgical clip during formation of a subsequent surgical clip about tissue adjacent to the previously formed surgical clip.

In one embodiment, the surgical clip applier further includes a handle assembly and a shaft extending distally from the handle assembly. The jaw assembly is disposed at a distal end of the shaft.

In another embodiment, each surgical clip includes a pair of legs interconnected by a backspan.

In another embodiment, the opposed surfaces of the jaws each define a clip track therein. The clip tracks are configured to guide translation of the legs of the surgical clip therealong as the jaws are moved from the spaced-apart position to the approximated position to form the surgical clip about tissue.

In still another embodiment, the relief recess is configured to receive the backspan of the previously formed surgical clip therein. More specifically, the relief recess may be shaped complementary to at least a portion of the surgical clip, e.g., the backspan of the surgical clip.

In yet another embodiment, the relief elements of the jaws each define at least a portion of the relief recess such that the portions of the relief recess cooperate with one another upon approximation of the jaw members to define the complete relief recess.

In still yet another embodiment, the relief elements each define an angled cam surface on an outwardly-facing surface thereof. The angled cam surfaces are configured to facilitate movement of the jaws to the approximated position.

A surgical jaw assembly for use in a surgical clip applier is also provided in accordance with an embodiment of the present disclosure. The surgical jaw assembly is adapted to store and fire a plurality of surgical clips in succession. The surgical jaw assembly includes first and second opposed jaws, each defining an opposed surface configured to receive a portion of a surgical clip. The jaws are moveable between a spaced-apart position and an approximated position for forming the surgical clip about tissue. Each jaw includes a raised element defining an angled cam surface on an outwardly-facing surface thereof that is configured to facilitate movement of the jaws to the approximated position. The raised elements are cooperable with one another upon approximation of the jaw members to define the a relief recess. The relief recess is configured to receive at least a portion of a previously formed surgical clip during formation of a subsequent surgical clip about tissue adjacent to the previously formed surgical clip.

In embodiments, the surgical clips are configured similarly as described above. As such, the relief recess may be configured to receive the backspan of the previously formed surgical clip therein. Further, the relief recess may be shaped complementary to the at least a portion of the previously formed surgical clip.

In another embodiment, the raised elements are disposed on surfaces adjacent to and substantially transverse relative to the opposed surface of the jaw thereof.

In still yet another embodiment, the raised elements each define at least a portion of the relief recess such that, upon approximation of the jaws, the portions of the relief recess cooperate to form the full relief recess.

A method of applying a plurality of surgical clips to tissue is also provided in accordance with the present disclosure. The method includes providing a surgical clip applier (or jaw assembly thereof) according to any of the embodiments above. Next, the jaws are positioned such that tissue is disposed therebetween and are moved from the spaced-apart position to the approximated position to form a first surgical clip about tissue. Thereafter, the jaws are positioned adjacent to the first surgical clip such that tissue is disposed between the jaws and are moved from the spaced-apart position to the approximated position to form a second surgical clip about tissue adjacent the first surgical clip and such that at least a portion of the first surgical clip is received within the relief recess during formation of the second surgical clip.

BRIEF DESCRIPTION OF THE DRAWINGS

Various embodiments of the subject instrument are described herein with reference to the drawings wherein:

FIG. 3B is an enlarged, bottom, perspective view of the jaws of the surgical clip applier of FIGS. 1-2 shown with a previously formed surgical clip disposed within a relief feature of the jaws;

FIG. 3C is a bottom, perspective view illustrating a driver assembly moving the jaw assembly to an approximated position;

FIG. 4A is a longitudinal, cross-sectional view of the jaw assembly, as taken through 4A-4A of FIG. 3B;

FIG. 4B is a transverse, cross-sectional view of the jaw assembly, as taken through 4B-4B of FIG. 3B;

DETAILED DESCRIPTION

Figure 1:
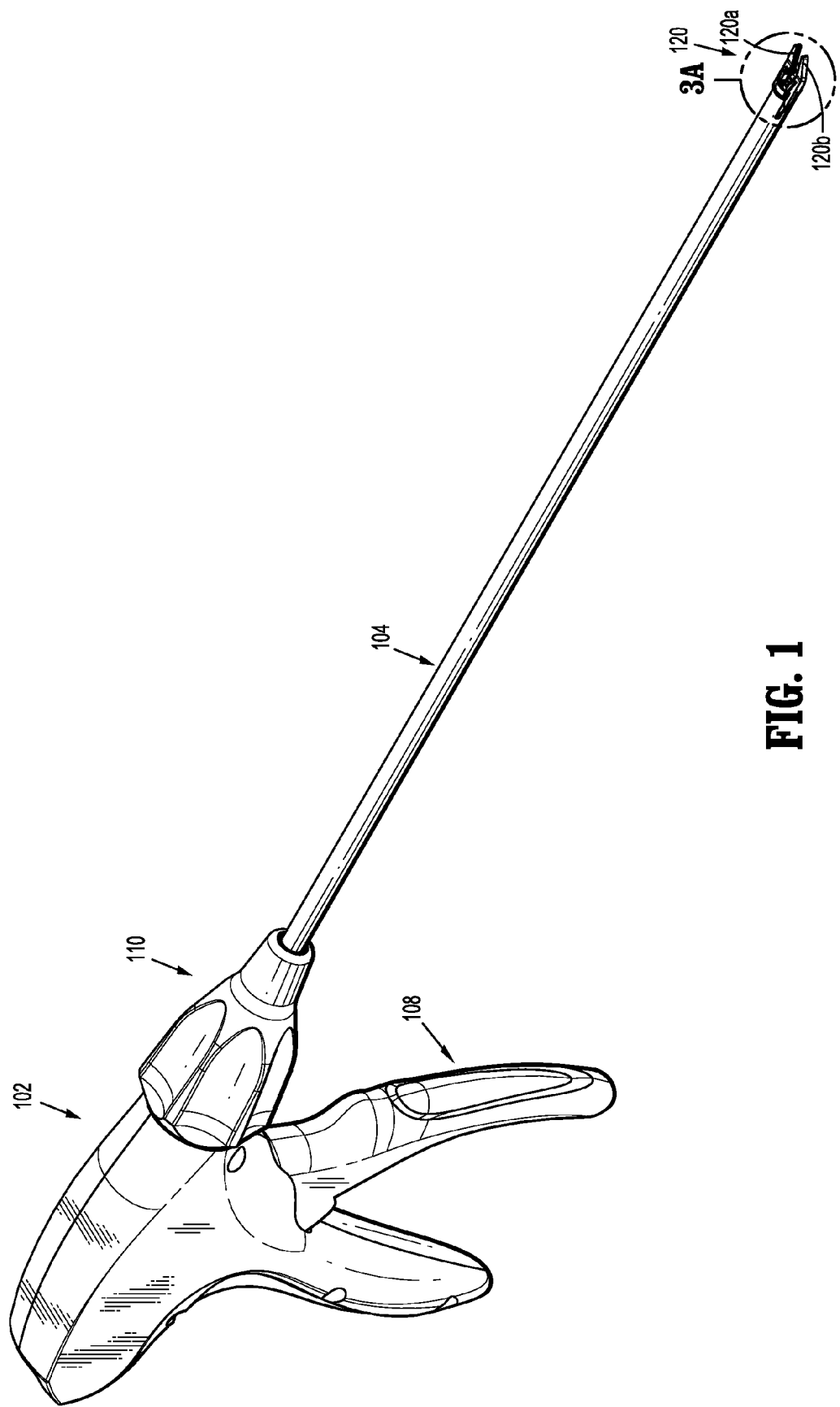
FIG. 1 is a perspective view of a surgical clip applier.

Embodiments of a surgical clip applier in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figures 2, 3A:
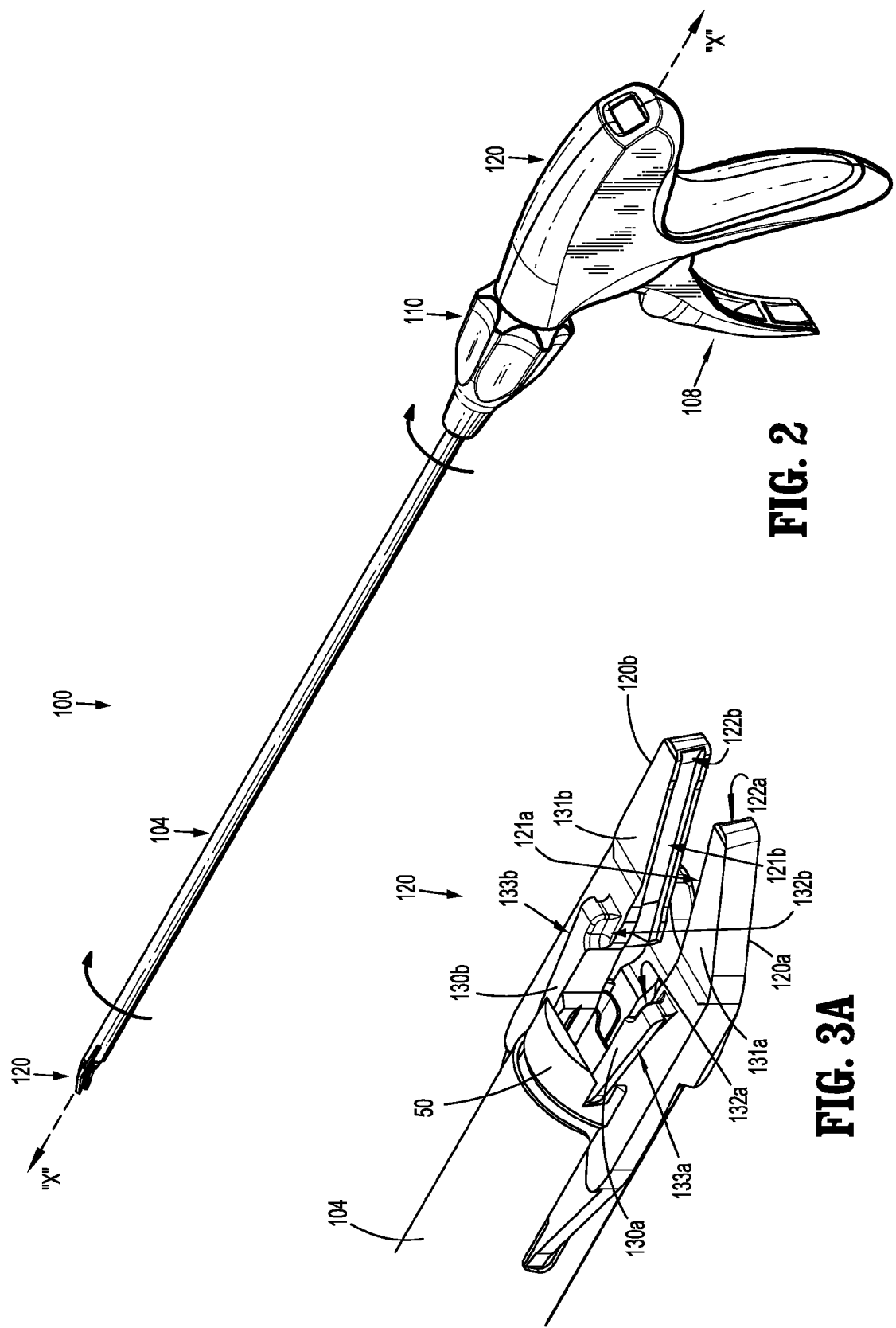
FIG. 2 is a further perspective view of the surgical clip applier of FIG. 1, illustrating a rotation of a shaft thereof.
FIG. 3A is an enlarged, bottom, perspective view of the jaw assembly of the surgical clip applier of FIGS. 1-2.

Referring to FIGS. 1-2, a surgical clip applier in accordance with the present disclosure is generally designated as 100. Surgical clip applier 100 generally includes a handle assembly 102 and an endoscopic portion including a shaft assembly 104 extending distally from handle assembly 102 and having a jaw assembly 120 disposed at a distal end thereof. A stack of surgical clips (not explicitly shown) is typically loaded and/or retained within shaft assembly 104 in a manner so as to slide therewithin and/or therealong. A complete description of the inner-workings and operation of surgical clip applier 100 can be found in commonly-assigned U.S. patent application Ser. No. 12/055,446 to Whitfield et. al., the entire contents of which are hereby incorporated by reference herein.

With continued reference to FIGS. 1-2, jaw assembly 120 is mounted in the distal end of shaft assembly 104 such that jaws 120a, 120b are longitudinally stationary relative thereto. A knob 110 may be rotatably mounted on a distal end of handle assembly 102 and affixed to shaft assembly 104 to transmit and/or provide 360° rotation to shaft assembly 104 and jaws 120a, 120b about a longitudinal axis "X-X" thereof. As will be described in greater detail hereinbelow, jaws 120a and 120b of jaw assembly 120 are each configured to guide passage of a surgical clip "C" (FIG. 5) therethrough and are moveable relative to one another from a spaced-apart position (FIG. 3A) and an approximated position (FIG. 3B-3C) to crimp, or form the surgical clip "C" (FIG. 5) about tissue.

Turning now to FIGS. 3A-4B, jaws 120a, 120b of jaw assembly 120 each define a respective clip track 122a, 122b within an inwardly facing, or opposed surface 121a, 121b, respectively, thereof. Clip tracks 122a, 122b are configured to receive surgical clip "C" therethrough as jaws 120a, 120b are moved to the approximated position to form the surgical clip "C" about tissue disposed between jaws 120a, 120b. Further, each jaw includes a raised element 130a, 130b, respectively, disposed on an adjacent, transverse surface 131a, 131b thereof relative to opposed surfaces 121a, 121b, respectively. For example, in the orientation of jaw assembly 120 shown in FIGS. 3A-3C, opposed surfaces 121a, 121b, respectively, are positioned as inwardly-facing "side" surfaces, while the raised elements 130a, 130b are disposed on the adjacent and transversely-positioned "upper" surfaces 131a, 131b of jaws 120a, 120b, respectively. As can be appreciated, given that jaw assembly 120 may be rotated, e.g., via rotating knob 110 (FIG. 1) and/or by simply rotating the entire surgical clip applier 100 (FIG. 1), these orientation-indicating markers, e.g., upper, lower, and side, will not necessarily remain the same. However, the positioning of surfaces 121a, 121b and surfaces 131a, 131b adjacent to and transverse relative to one another will remain constant regardless of the orientation of jaw assembly 120.

With continued reference to FIGS. 3A-4B, raised elements 130a, 130b each include a distally and inwardly-facing recess 132a, 132b, respectively, defined therein. Recesses 132a, 132b are configured such that, upon approximation of jaws 120a, 120b, as best shown in FIG. 3B, recesses 132a, 132b cooperate with one another to form a combined recess 132. Recess 132 defines a generally horseshoe or u—shaped configuration, although other configurations are contemplated.

More specifically, recess 132 is configured to define a complementary-shaped configuration to that of backspan 220c of surgical clip "C" when surgical clip "C" is formed about tissue such that, as will be described in greater detail below, back span 220c of surgical clip "C" is capable of being received therein. As such, a diameter or width of recess 132 may be slightly larger that that of a formed surgical clip "C" such that a formed surgical clip "C" is receivable therein, but not too large such that substantial movement of the formed surgical clip "C," when disposed therein, is inhibited.

Further, depending on the configuration of the surgical clip "C" used, the configuration of recess 132 may be altered accordingly, i.e., to maintain complementary-shaped configurations. For example, recess 132 may define a "V"-shaped configured for use with surgical clips having a "V"-shaped backspan in the formed condition. As will be described in greater detail below, and as shown in FIGS. 4A-4B, recess 132, formed via cooperation of recesses 132a, 132b of raised elements 130a, 130b of jaws 120a, 120b, upon approximation of jaws 120a, 120b, is configured to receive or retain an end of a previously formed surgical clip "C1" therein, while a second surgical clip "C2" is guided through clip tracks 122a, 122b of jaws 120a, 120b, respectively, as jaw members 120a, 120b are moved to the approximated position to form the second surgical clip "C2" about tissue in position adjacent the first, or previously formed surgical clip "C1."

Referring now to FIG. 3C, raised elements 130a, 130b, disposed on surfaces 131a, 131b of jaws 120a, 120b, respectively, help impart an increased closing force to jaws 120a, 120b, thereby facilitating approximation of jaws 120a, 120b. More particularly, raised elements 130a, 130b each include an outwardly-facing, angled cam surface 133a, 133b tapering inwardly in a proximal direction. In use, upon actuation of jaws 120a, 120b, e.g., via depression of trigger 108, cam driver 50 is translated distally relative to jaws 120a, 120b, ultimately contacting angled cam surfaces 133a, 133b of raised elements 130a, 130b, respectively. Due to the distally and outwardly sloped angled surfaces 133a, 133b, of raised elements 130a, 130b, respectively, as cam driver 50 is translated further distally, raised elements 130a, 130b and, thus, jaws 120a, 120b are urged into approximation with one another. In the approximated position, as best shown in FIGS. 3B and 3C, raised elements 130a, 130b are disposed in close proximity to one another such that relief recesses 132a, 132b, respectively, thereof cooperate to form recess 132, the additional importance of which will be described in greater detail below.

Figure 5:
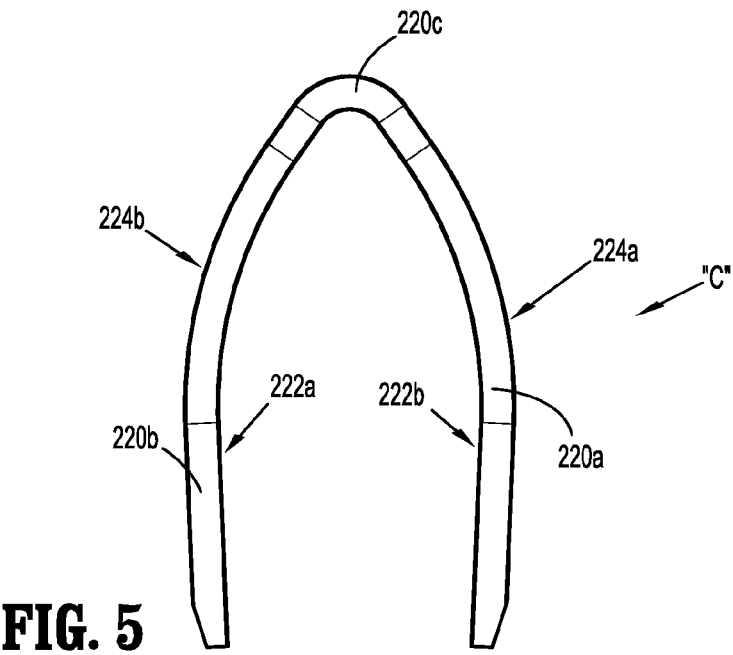
FIG. 5 is a top view of a surgical clip for use with the surgical clip applier of FIGS. 1-2.

Referring now to FIG. 5, a typical surgical clip "C" configured for use with surgical clip applier 100 (FIG. 1) is shown. Clip "C" includes a pair of legs 220a, 220b interconnected by a crown, crossbar, or backspan 220c. An inwardly facing surface 222a, 222b of each leg 220a and 220b, respectively, defines a generally flat geometry such that upon forming of clip "C" about a body tissue or vessel, inwardly facing surfaces 222a and 222b of legs 220a and 220b consistently and evenly clamp around the body tissue or vessel. Outwardly facing surfaces 224a and 224b of legs 220a and 220b, respectively, may define a generally circular transverse cross-sectional configuration, or any other suitable configuration. In particular, outwardly-facing surfaces 224a and 224b may be shaped complementarily to clip tracks 122a, 122b to facilitate translation through clip tracks 122a, 122b as jaws 120a, 120b are moved to the approximated position to form clip "C" about tissue. Backspan 220c may be configured similarly to legs 220a, 220b to form a substantially consistent configuration along the entire outwardly facing surface of clip "C," although other configurations are contemplated.

The operation of surgical clip applier 100, to crimp, form, or form a plurality of surgical clips "C1" and "C2" about a target body tissue, e.g., a vessel "V" (FIGS. 6-10), in close proximity, i.e., adjacent, to one another will now be described with reference to FIGS. 1-10.

Figure 6:
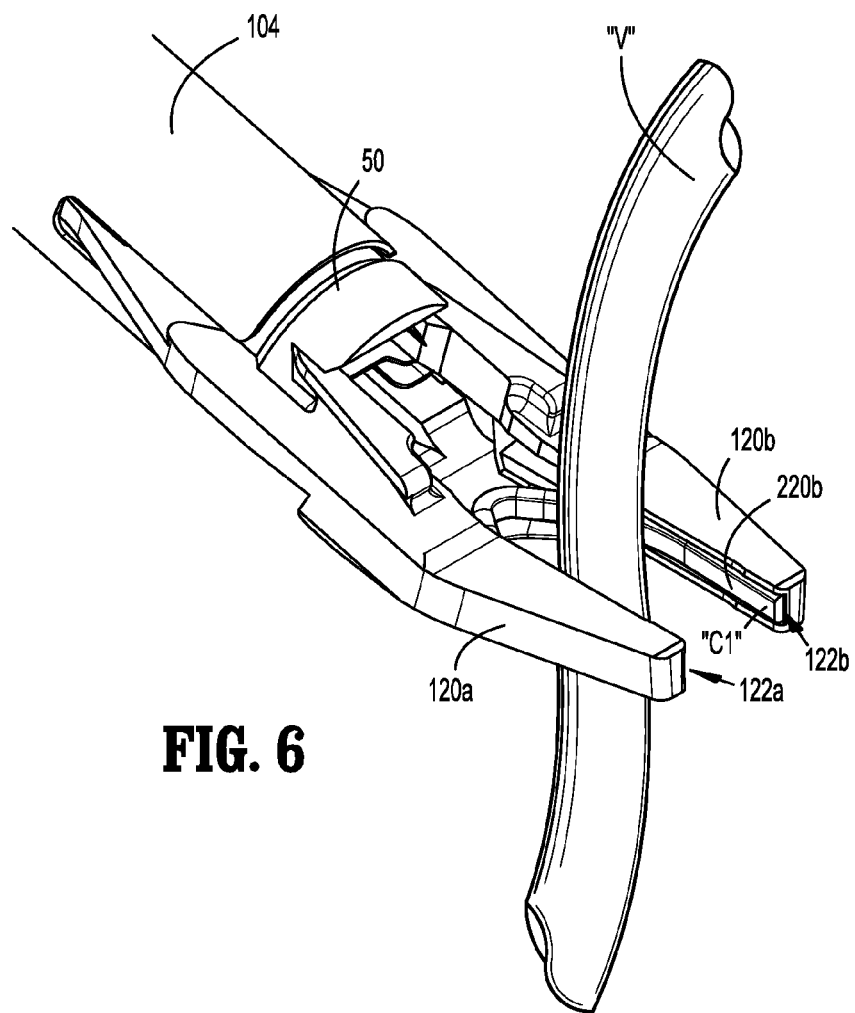
FIGS. 6-10 illustrate a use of the surgical clip applier of FIGS. 1-5 in applying a series of surgical clips to a target surgical site.

Initially, as seen in FIG. 6, clip applier 100 is positioned such that a tissue or a vessel "V" to be clamped is disposed between jaws 120a and 120b. As trigger 108 is squeezed or actuated, trigger 108 causes clip "C1" to translate distally into clip tracks 122a and 122b of opposed surfaces 121a, 121b of jaws 120a and 120b, respectively, such that at least a portion of leg 220a of clip "C1" is positioned within clip track 122a of jaw member 120a and such that at least a portion of leg 220b of clip "C1" is positioned within clip track 122b of jaw member 120b. Thus, legs 220a and 220b of clip "C1," similar to jaws 120a and 120b, are now also positioned surrounding tissue or vessel "V" to be clamped.

As trigger 108 is squeezed further, jaws 120a and 120b are moved from the spaced-apart position toward the approximated position, thereby beginning to form surgical clip "C1" therebetween. As discussed above, upon actuation of trigger 108, cam driver 50 is translated distally into contact with angled cam surfaces 133a, 133b of raised elements 130a, 130b to facilitate movement of jaws 120a, 120b to the approximated position. During formation of clip "C1," the flat, inwardly facing surfaces 222a and 222b of legs 220a and 220b of clip "C1" are approximated toward each other to thereby effect clamping of vessel "V." Alternatively, inwardly facing surfaces 222a, 222b may include one or more features to promote a secure and effective clamp about tissue or vessel "V." Once clip "C1" has been clamped about vessel "V," as shown in FIG. 7, trigger 108 may be released, allowing jaw assembly 120 to return back to the spaced-apart position.

Figure 7:
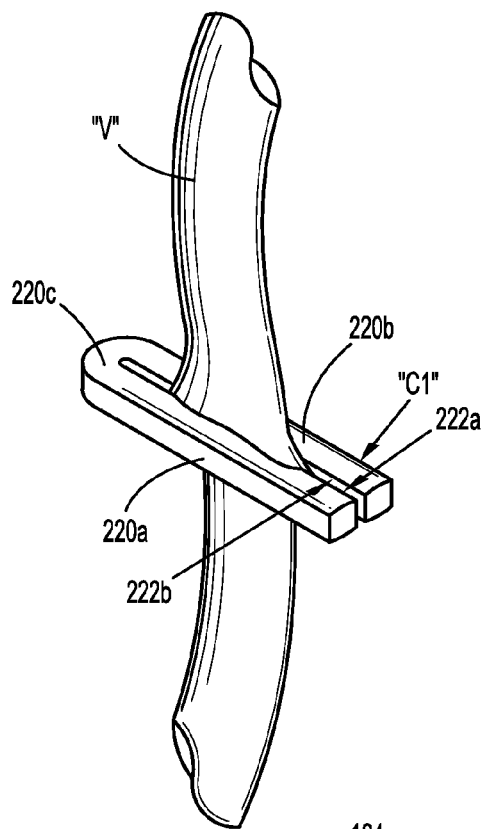
Figure 8:
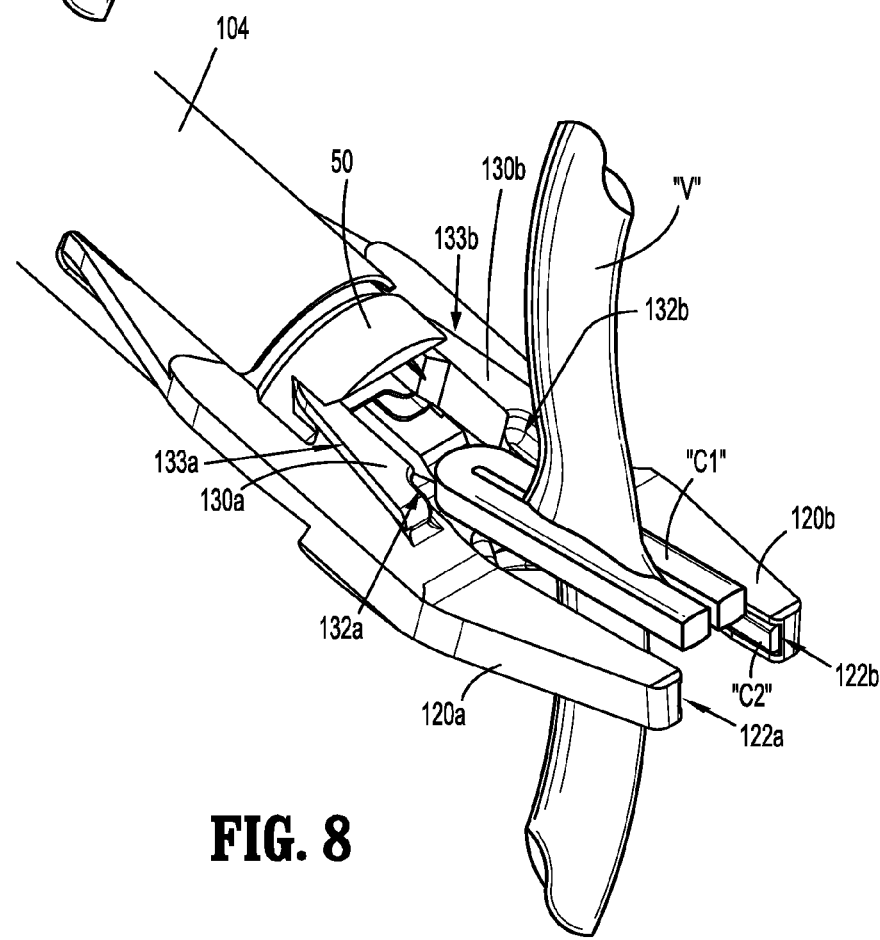
Figure 9:
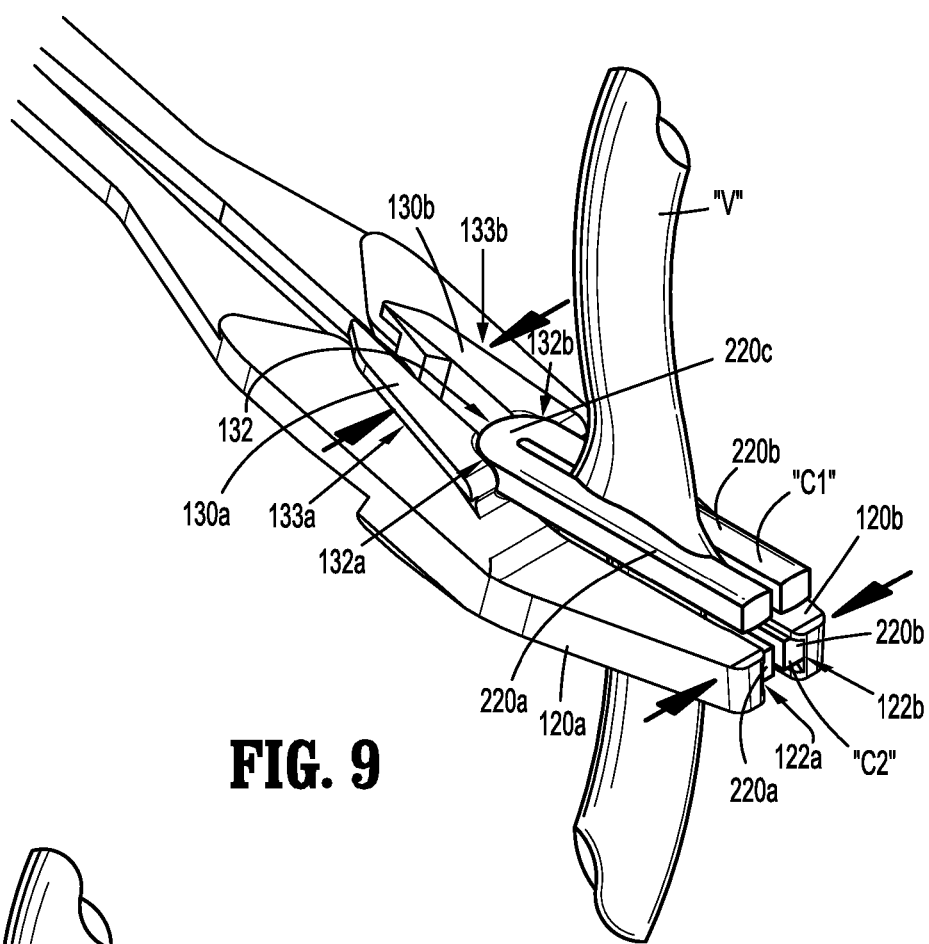

Once the first clip "C1" has been formed about vessel "V," as shown in FIG. 7, a second clip "C2" may be formed about vessel "V" adjacent to first clip "C1." In order to apply second clip "C2", clip applier 100 is once again positioned such that vessel "V" is disposed between jaws 120a and 120b, directly adjacent the previously-formed first clip "C1," as shown in FIG. 8. Once in position, trigger 108 is squeezed causing clip "C2" to translate distally into clip tracks 122a and 122b and, ultimately, to be formed about vessel "V" as jaws 120a and 120b are moved from the spaced-apart position to the approximated position.

During approximation of jaws 120a, 120b to form clip "C2" about tissue, as best shown in FIGS. 3B, 4A-4B and 9, raised elements 130a, 130b are approximated relative to one another. More specifically, as raised elements 130a, 130b are approximated relative to one another, backspan 220c of clip "C1" is received within recess 132 formed by the approximation of recesses 132a, 132b of raised elements 130a, 130b, respectively. Accordingly, raised elements 130a, 130b and, thus, jaws 120a 120b are permitted to move to the fully approximated position, while backspan 220c of surgical clip "C1" is received within recess 132 of jaw assembly 120. In other words, recess 132 provides a relief, or cut-out such that backspan 220c of formed clip "C1" does not interfere with the approximation of raised elements 130a, 130b during formation of second clip "C2."

As can be appreciated, this configuration permits formation of clips "C1" and "C2" in close proximity to one another while inhibiting dislodging or deformation of first clip "C1" and also helping to ensure that second clip "C2" is adequately and properly formed about vessel "V." In particular, with backspan 220c of first surgical clip "C1" retained within recess 132 of jaw assembly 120, first surgical clip "C1" remains displaced from the inter-jaw space as well as the space between raised elements 130a, 130b, thus allowing jaws 120a, 120b to fully approximate, ensuring adequate application of second surgical clip "C2" about tissue and inhibiting damage to or malformation of clips "C1" or "C2" and/or surgical clip applier 100 that may result from first surgical clip "C1" interfering with the movement of jaws 120a, 120b and/or the advancement of second surgical clip "C2" therethrough during a placement/formation of second surgical clip "C2" adjacent and in close proximity to first surgical clip "C1."

Figure 10:
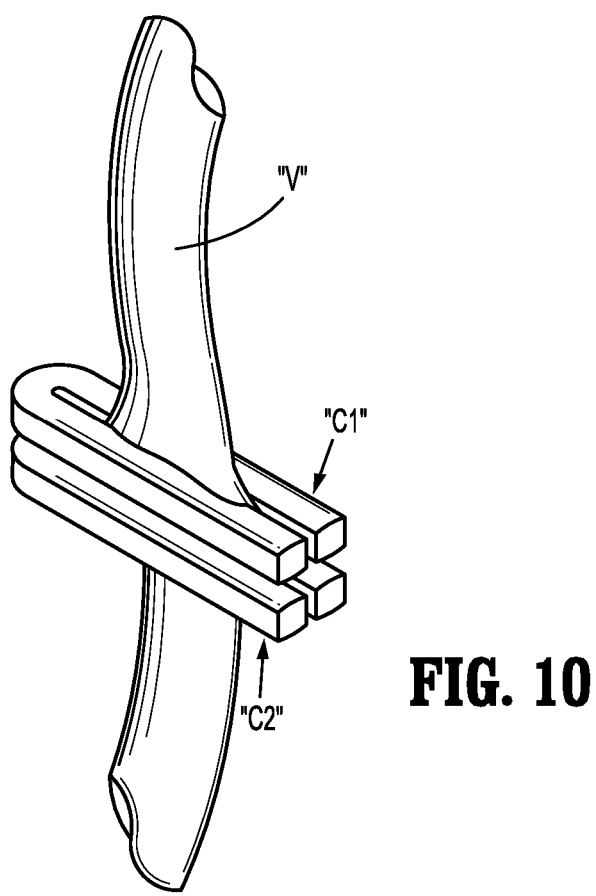

Once second clip "C2" has been clamped about vessel "V," as shown in FIG. 10, trigger 108 may be released, allowing jaw assembly 120 to return back to the spaced-apart position. Subsequent clips "C" may then be applied similarly as described above.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
   a jaw assembly including first and second jaws, each jaw defining an opposed surface configured to receive a portion of a surgical clip, the jaws moveable between a spaced-apart position and an approximated position for forming the surgical clip about tissue, each jaw including a relief element disposed on a surface adjacent to and substantially transverse relative to the opposed surface thereof, each relief element movable with the respective jaw thereof relative to the other jaw and the relief element thereof, each relief element defining a relief recess portion therein having an arcuate configuration such that, upon movement of the jaws to the approximated position, the relief recess portions cooperate to form a relief recess defining a U-shaped configuration configured to complimentarily receive a U-shaped portion of a previously formed surgical clip during formation of a subsequent surgical clip about tissue adjacent the previously formed surgical clip.

2. The surgical clip applier according to claim 1, further comprising a handle assembly and a shaft extending distally from the handle assembly, the jaw assembly disposed at a distal end of the shaft.

3. The surgical clip applier according to claim 1, wherein each surgical clip includes a pair of legs interconnected by a backspan.

4. The surgical clip applier according to claim 3, further comprising a clip track defined within the opposed surface of each of the jaws, the clip tracks configured to guide translation of the legs of the surgical clip therealong as the jaws are moved from the spaced-apart position to the approximated position to form the surgical clip about tissue.

5. The surgical clip applier according to claim 3, wherein the relief recess is configured to complimentarily receive the backspan of the previously formed surgical clip therein, the backspan of the previously-formed surgical clip defining the U-shaped portion of the previously formed surgical clip.

6. The surgical clip applier according to claim 1, wherein the relief elements each define an angled cam surface on an outwardly-facing surface thereof, the angled cam surfaces configured to facilitate movement of the jaws to the approximated position.

7. A surgical clip applier adapted to store and fire a plurality of surgical clips in succession, the surgical clip applier comprising:
   a cam driver; and
   first and second opposed jaws, each jaw defining an opposed surface configured to receive a portion of a surgical clip, the jaws moveable relative to one another, in response to urging from the cam driver, between a spaced-apart position and an approximated position for forming the surgical clip about tissue, each jaw including a raised element disposed thereon and movable with the respective jaw thereof relative to the other jaw and the raised element thereof between the spaced-apart position and the approximated position, each raised element defining an angled cam surface on an outwardly-facing surface thereof, wherein the cam driver is configured to contact and cam along the angled cam surfaces to facilitate movement of the jaws to the approximated position, the raised elements cooperable with one another upon approximation of the jaw members to define a relief recess having a U-shaped configuration, the relief recess configured to complimentarily receive a U-shaped portion of a previously formed surgical clip during formation of a subsequent surgical clip about tissue adjacent to the previously formed surgical clip.

8. The surgical clip applier according to claim 7, wherein each surgical clip includes a pair of legs interconnected by a backspan.

9. The surgical clip applier according to claim 8, wherein the relief recess is configured to complimentarily receive the backspan of the previously formed surgical clip therein, the backspan of the previously-formed surgical clip defining the U-shaped portion of the previously formed surgical clip.

10. The surgical clip applier according to claim 7, wherein each raised element is disposed on a surface adjacent to and substantially transverse relative to the opposed surface of the jaw thereof.

11. The surgical clip applier according to claim 7, wherein the raised elements of the jaws each define at least a portion of the relief recess, the portions of the relief recess cooperating to define the relief recess upon movement of the jaws to the approximated position.

12. A method of applying a plurality of surgical clips to tissue, the method comprising:
   providing a jaw assembly including first and second jaws defining opposed surfaces configured to receive a surgical clip therebetween, each jaw including a relief element disposed on a surface adjacent to and substantially traverse relative to the opposed surface thereof, the relief elements movable relative to one another in response to movement of the jaws relative to one another such that the relief elements cooperate to define a relief recess in an approximated position of the jaws, the relief recess defining a U-shaped configuration;
   positioning the jaws such that tissue is disposed therebetween;
   moving the jaws from a spaced-apart position to the approximated position to form a first surgical clip about tissue;
   positioning the jaws adjacent to the first surgical clip and such that tissue is disposed between the jaws; and
   moving the jaws from the spaced-apart position to the approximated position to form a second surgical clip about tissue adjacent the first surgical clip such that a U-shaped portion of the first surgical clip is complimentarily received within the relief recess during formation of the second surgical clip.

13. The method according to claim 12, wherein the first and second surgical clips each include a pair of legs interconnected by a backspan, the backspan of the first surgical clip defining the U-shaped portion thereof.

14. The method according to claim 13, wherein the legs of each surgical clip translate along guide tracks defined within the opposed surfaces of the jaws as the jaws are moved from the spaced-apart position to the approximated position to form the surgical clip about tissue.

15. The method according to claim 12, wherein the relief elements each define an angled cam surface on an outwardly-facing surface thereof, the angled cam surfaces configured to facilitate movement of the jaws to the approximated position.

16. The method according to claim 12, wherein the relief elements of the jaws each define at least a portion of the relief recess such that moving the jaws to the approximated position moves the portions of the relief recess into cooperation with one another to define the relief recess.

\* \* \* \* \*